United States Patent
Lindner (10) Patent No.: US 9,452,275 B2
(45) Date of Patent: Sep. 27, 2016

(54) DETACHABLE INSPIRATORY RELIEF VALVE

(71) Applicant: General Electric Company, Schenectady, NY (US)

(72) Inventor: Doron Lindner, Haifa (IL)

(73) Assignee: General Electric Company, Schenectady, NY (US)

( * ) Notice: Subject to any disclaimer, the term of this patent is extended or adjusted under 35 U.S.C. 154(b) by 950 days.

(21) Appl. No.: 13/723,324

(22) Filed: Dec. 21, 2012

(65) Prior Publication Data

US 2014/0174445 A1   Jun. 26, 2014

(51) Int. Cl.
*A61M 16/20* (2006.01)
*A61M 16/08* (2006.01)

(52) U.S. Cl.
CPC ........... *A61M 16/201* (2014.02); *A61M 16/20* (2013.01); *A61M 16/204* (2014.02); *A61M 16/0816* (2013.01); *A61M 16/0875* (2013.01); *A61M 16/209* (2014.02)

(58) Field of Classification Search
CPC ............. A61M 16/20; A61M 16/201; A61M 16/204; A61M 16/206; A61M 16/209; A61M 16/00; A61M 16/0875; A61M 16/08; A62B 9/02
USPC ............... 128/205.24; 137/493, 493.8, 614.2
See application file for complete search history.

(56) References Cited

U.S. PATENT DOCUMENTS

| 3,933,171 | A | * | 1/1976 | Hay ..................... A61M 16/208 128/205.24 |
|---|---|---|---|---|
| 4,823,828 | A | | 4/1989 | McGinnis |
| 5,127,400 | A | | 7/1992 | DeVries et al. |
| 6,102,038 | A | | 8/2000 | DeVries |
| 6,343,603 | B1 | | 2/2002 | Tuck et al. |
| 7,464,710 | B2 | | 12/2008 | Nguyen |
| 8,118,024 | B2 | | 2/2012 | DeVries et al. |
| 8,205,451 | B2 | | 6/2012 | Narayan et al. |
| 2007/0017207 | A1 | | 1/2007 | Smith et al. |
| 2011/0168180 | A1 | | 7/2011 | Lugtigheid |
| 2013/0118499 | A1 | | 5/2013 | Parr et al. |

FOREIGN PATENT DOCUMENTS

| CN | 201888980 U | 7/2011 |
|---|---|---|
| EP | 1177808 A1 | 2/2002 |
| FR | 2535612 A1 | 5/1984 |

OTHER PUBLICATIONS

Unofficial English translation of Chinese Office Action issued in connection with corresponding CN Application No. 201310713646.X on Jul. 21, 2015.

* cited by examiner

*Primary Examiner* — Justine Yu
*Assistant Examiner* — Colin W Stuart
(74) *Attorney, Agent, or Firm* — Andrus Intellectual Property Law, LLP (57) ABSTRACT

A relief valve assembly for use with a ventilator to selectively release pressure from within a breathing tube. The relief valve assembly can be attached and removed from the ventilator as a single unit. The relief valve assembly includes a sealing member that is movable by operating components within the ventilator to either seal or open at least one relief port contained within the relief valve assembly.

20 Claims, 9 Drawing Sheets

DETACHABLE INSPIRATORY RELIEF VALVE

BACKGROUND

The present disclosure generally relates to an inspiratory relief valve for use with a ventilator. More specifically, the present disclosure relates to a detachable relief valve assembly that can be removed from a ventilator for disinfection/sterilization while providing automatic pressure relief.

Ventilators currently exist to provide a supply of breathing gas at pressure to a patient to either supplement the patient's breathing or to provide the full breathing function for the patient depending upon the condition of the patient. Breathing gas is provided to the patient through a breathing tube connected to the ventilator. Typically, the ventilator includes an inspiratory port that interfaces with the breathing tube directing the breathing gas to the patient. An interface on the ventilator provides the point of connection for the breathing tube and the inspiratory port. Typically, the interface between the breathing tube and the inspiratory port is a simple mechanical connection that allows breathing gas to securely pass from the inspiratory port to the breathing tube.

Various standards have been proposed and adopted that call for the automatic relief of pressure in the patient's lungs if an occlusion should occur. In addition, requirements have been proposed that require that the entire gas path to the patient must be able to be disinfected/sterilized or designed to be immune from contamination. Therefore, a need exists for designs that both provide the automatic relief of pressure in the patient's lungs along with designs that can be readily disinfected and/or sterilized.

BRIEF DESCRIPTION

The present disclosure relates to an inspiratory relief valve that can be installed and removed from a ventilator as a single unit. The relief valve assembly can be removed from the ventilator and disinfected/sanitized when desired.

The relief valve assembly of the present disclosure is designed for use with a ventilator that has an inspiratory port for delivering breathing gas to a patient. The relief valve assembly includes a connector housing that includes an attachment feature that allows the relief valve assembly to be removably attached to the ventilator. Preferably, the attachment feature engages a locking ring on the ventilator to removably attach the relief valve assembly to the ventilator.

The connector housing includes an engagement tube that is received in the relief port of the ventilator such that a breathing gas from the inspiratory port flows into the engagement tube. A connector tube of the connector housing surrounds a distal end of the engagement tube such that gas from within the engagement tube flows into the connector tube. The connector tube is sized to receive a breathing tube to deliver breathing gas to the patient.

At least one relief port is formed in the connector housing between the connector tube and the engagement tube. The relief ports allow gas to flow out of the connector tube to atmosphere without returning to the ventilator through the engagement tube. A sealing member is selectively movable into and out of contact with the relief ports to control the flow of breathing gas out of the connector housing through the relief ports. The position of the sealing member is controlled by the ventilator to selectively provide a pressure relief for gas within the breathing tube.

The connector housing further includes a one-way valve positioned at the distal end of the engagement tube to permit one-way flow of breathing gas from the engagement tube to the connector tube. The one-way valve is a flap valve that prevents the back flow of breathing gas to the ventilator.

The sealing member is biased into an engagement position to restrict the flow of gas through the relief ports. The movement of the sealing member away from the relief ports allows breathing gases to be vented to atmosphere through the relief ports.

The relief valve assembly is formed as part of an interface assembly that is used between an inspiratory port of the ventilator and the breathing tube. The interface assembly includes an adjustment collar that is contained within the ventilator and selectively movable between a first position and a second position. The movement of the adjustment collar controls the position of the sealing member to selectively open and close the relief ports.

A bias force assembly is positioned to exert a bias force on the adjustment collar to urge the adjustment collar to the first, extended position in which the sealing member is forced into sealing engagement with the relief ports. A drive member in the ventilator is operable to move the adjustment collar to the second, retracted position against the bias force created by the bias spring. In this manner, the ventilator is able to control the selective opening and closing of the relief ports contained within the relief valve assembly.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
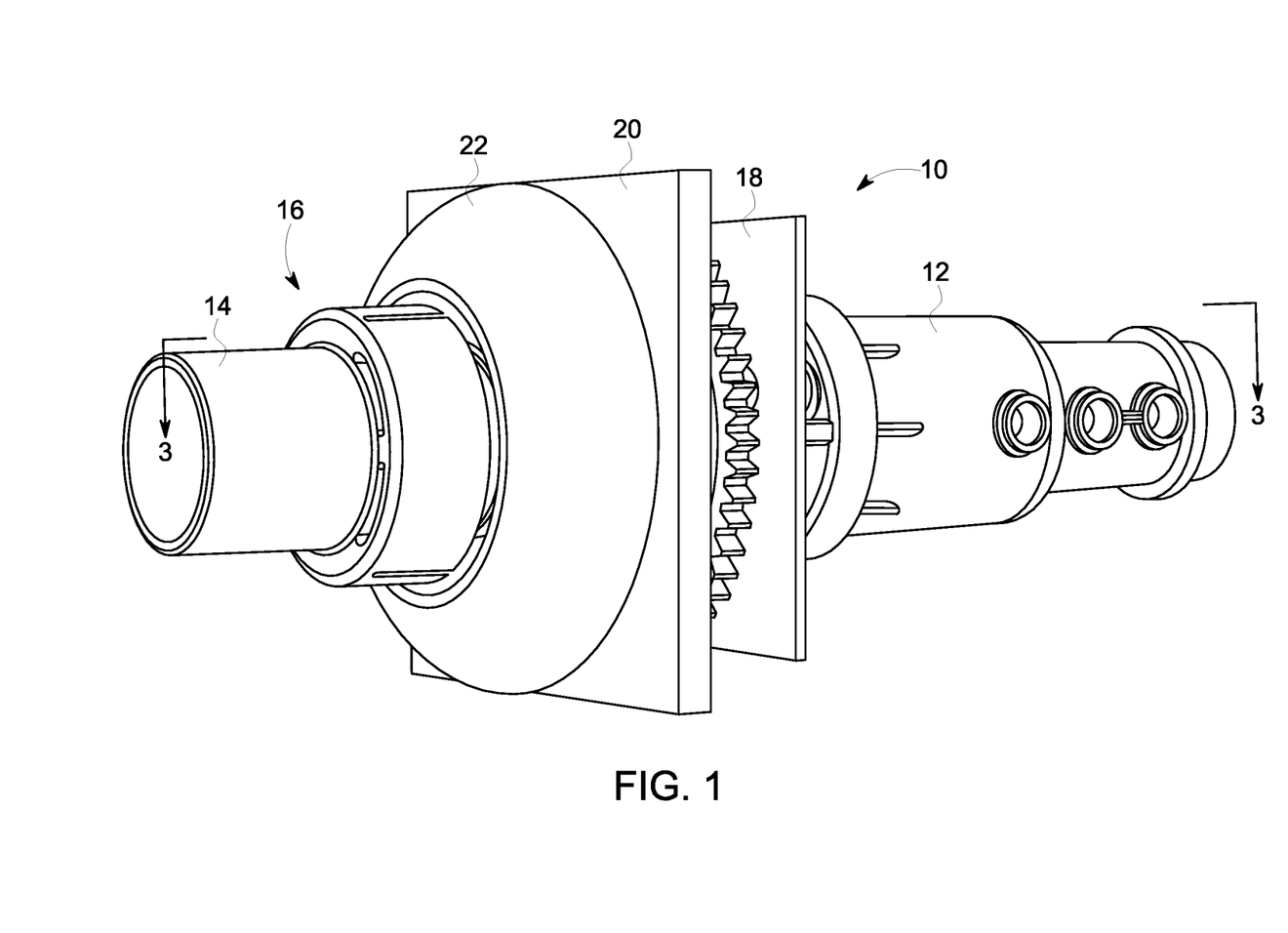
FIG. 1 is an isometric view of the detachable inspiratory relief valve as mounted to the inspiratory port of a ventilator.

FIG. 1 illustrates an interface assembly 10 for coupling an inspiratory port contained within a ventilator to a breathing tube that supplies a flow of breathing gas to a patient. The breathing tube, although not shown in FIG. 1, is designed to be connected to a connector tube 14 of a relief valve assembly 16 constructed in accordance with the present disclosure. The relief valve assembly 16 is shown in FIG. 1 in its connected position. However, the entire relief valve assembly 16 can be disconnected and separated from the ventilator as a single unit and subsequently disassembled for disinfecting/sanitizing.

In the illustration of FIG. 1, the pneumatic unit of the ventilator is illustrated by only a portion of an outer wall 18 typically formed from a metal material. In the illustration of FIG. 1, only a very small portion of the outer wall 18 of the pneumatic unit is shown but it should be understood that the pneumatic unit is a conventional portion of a ventilator. The ventilator further includes an outer housing 20 that surrounds the pneumatic unit and is typically formed from a plastic material. Once again, only a small portion of the outer housing 20 is shown in the illustration of FIG. 1. It should be understood that both the outer wall 18 and the outer housing 20 encase the ventilator in a known manner and provide access to the inspiratory port 12. In the embodiment shown in FIG. 1, a locking ring 22 is mounted to an outer surface of the outer housing 20 to provide a point of attachment for the relief valve assembly 16. Details of the engagement between the locking ring 22 and the relief valve assembly 16 will be described in much greater detail below.

Figure 2:
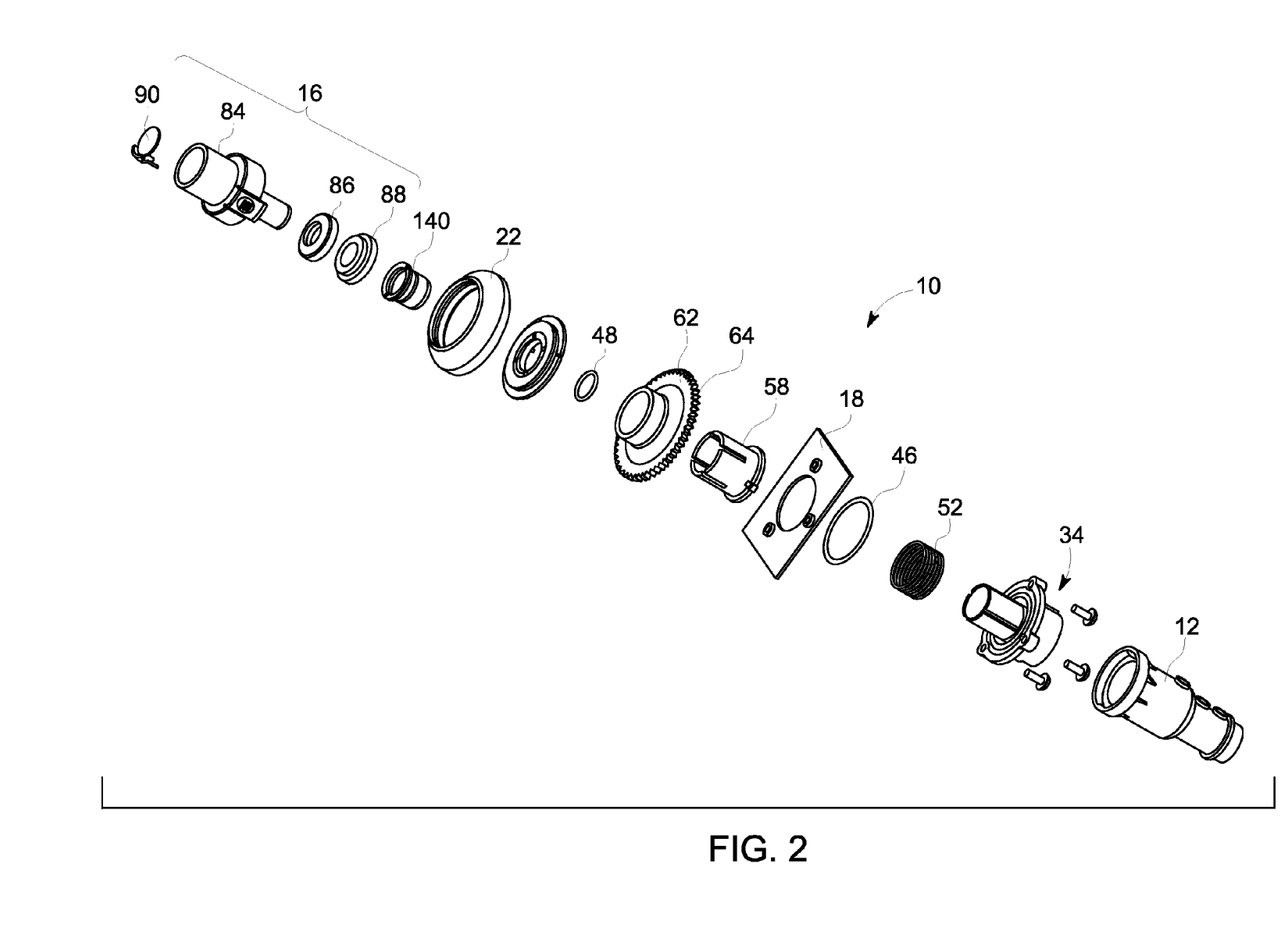
FIG. 2 is an exploded view showing the structural components of the detachable inspiratory relief valve and the operating element of the inspiratory port of the ventilator.

FIG. 2 of the present disclosure provides an exploded view of the components that form both the relief valve assembly 16 and the operating components of the ventilator. The reference numerals set forth in FIG. 2 are shown and described in the remaining Figures in the specification and FIG. 2 should be referred to for further illustration of the components to be described below.

Figure 3:
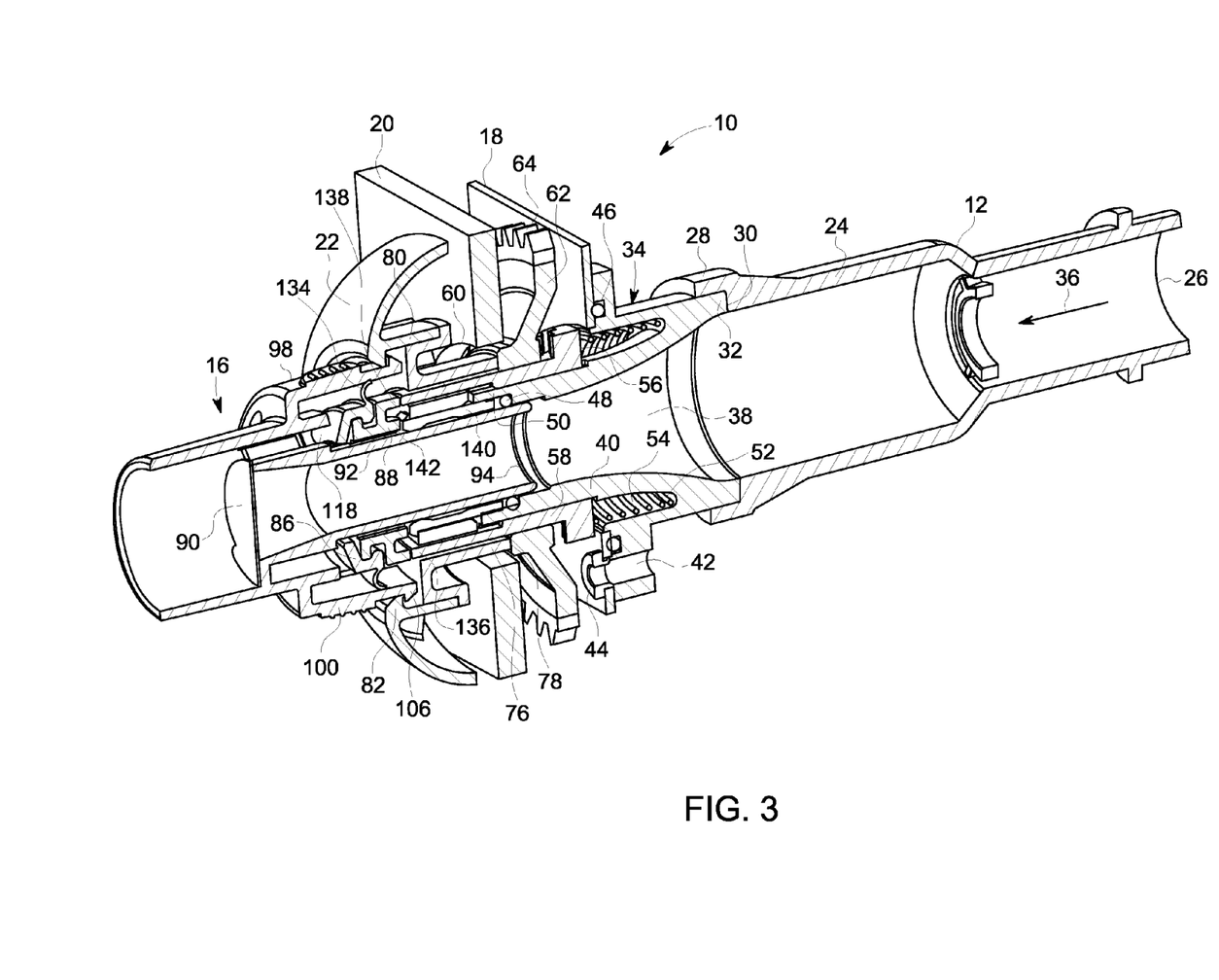
FIG. 3 is a section view taken along line 3-3 of FIG. 1.

Referring now to FIG. 3, the inspiratory port 12 of the ventilator includes a supply tube 24 that receives a flow of breathing gas from the ventilator at a first end 26. The supply tube 24 extends to a second end 28. The second end 28 includes a recessed shoulder 30 that receives a first end 32 of a bias force assembly 34. The first end 32 of the bias force assembly 34 is positioned in a fluid-tight arrangement with the second end 28 of the supply tube 24 to receive a flow of breathing gas from the ventilator, as shown by arrow 36. The flow of breathing gas enters into the open, second end of the bias force assembly 34 and flows through the open passageway 38 defined by outer wall 40. As illustrated in FIG. 3, the outer wall 40 extends through an opening formed in the metallic outer wall 18 of the pneumatic unit of the ventilator. The bias force assembly 34 is connected to the outer wall 18 by a series of connectors that pass through attachment bores 42 and are received within corresponding openings 44. A resilient sealing ring 46 provides a seal around the engagement between the bias force assembly 34 and an outer surface of the outer wall 18. A second sealing member 48 is located near a second end 50 of the bias force assembly 34.

As illustrated in FIG. 3, a bias spring 52 is entrapped within an open cavity 54 defined in the outer wall 40. The free end of the bias spring 52 engages an outer contact surface 56 of an adjustment collar 58. The adjustment collar 58 extends through an aligned opening 60 formed in the outer housing 20 of the ventilator. The adjustment collar 58 is designed to be movable relative to the stationary housing 20 between an extended first position and a retracted second position. The bias spring 52 provides a bias force on the contact surface 56 to bias the adjustment collar 58 toward a first position.

Figure 8:
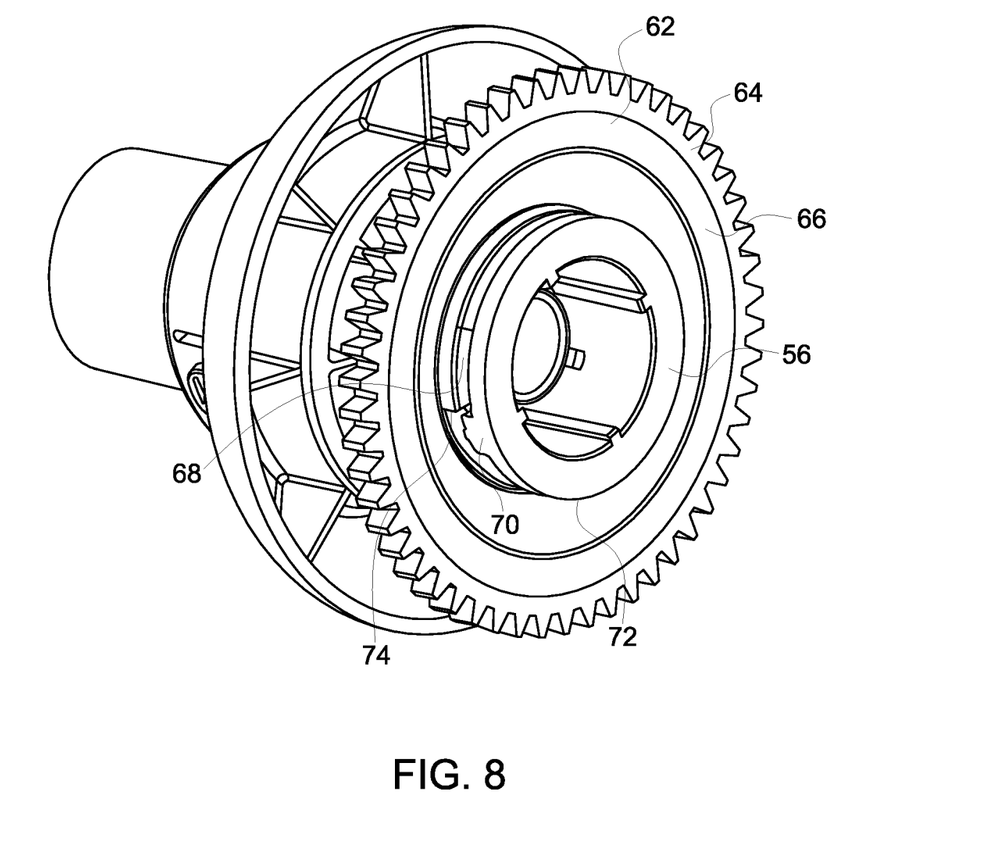
FIG. 8 is a back isometric view illustrating the interaction between the adjustment gear.

The interface assembly 10 further includes a drive disk 62 that is contained within the ventilator between the outer housing 20 and outer wall 18. The drive disk 62 includes a series of teeth 64 that engage a corresponding series of teeth of a drive assembly (not shown) contained within the ventilator. As can be seen in FIG. 8, a back face surface 66 of the drive disk 62 includes a sloping cam surface 68. The cam surface 68 interacts with a pair of extending tabs 70 that extend from the outer rim 72. The tabs 70 ride along the cam surface 68 such that when the drive disk 62 rotates, the movement of the tabs 70 along the cam surface 68 causes the adjustment collar 58 to compress the bias spring 52. Each of the cam surfaces 68 includes a shoulder 74. When the tab 70 is aligned with the shoulder 74, the bias spring is able to move the adjustment collar 58 to its first extended position. When the tab 70 is on the highest portion of the cam surface 68, the cam surface 68 compresses the bias spring and moves the adjustment collar to its retracted, second position. In this manner, the drive mechanism contained within the ventilator is able to rotate the drive disk 62 to selectively move the adjustment collar 58 between the extended first position and the retracted second position.

Referring back to FIG. 3, a mounting bracket 76 is supported on an outer face 78 of the drive disk 62 and extends through the opening 60 formed in the outer housing 20. The mounting bracket 76 receives an attachment portion 80 of the locking ring 22. The locking ring 22 and the mounting bracket 76 are stationary relative to the rotatable drive disk 62. As can be understood in FIG. 3, the adjustment collar 58 is movable relative to the stationary mounting bracket 76.

Locking ring 22 includes an inwardly extending projection 82 that provides a secure point of attachment for the relief valve assembly 16. The attachment between the relief valve assembly 16 and the locking ring 22 allows the relief valve assembly to be selectively attached to and removed from the ventilator. Although the locking ring 22 is shown in FIG. 3 as being the point of attachment to the ventilator, it is contemplated that various other attachment devices could be utilized while operating within the scope of the present disclosure.

Figure 4:
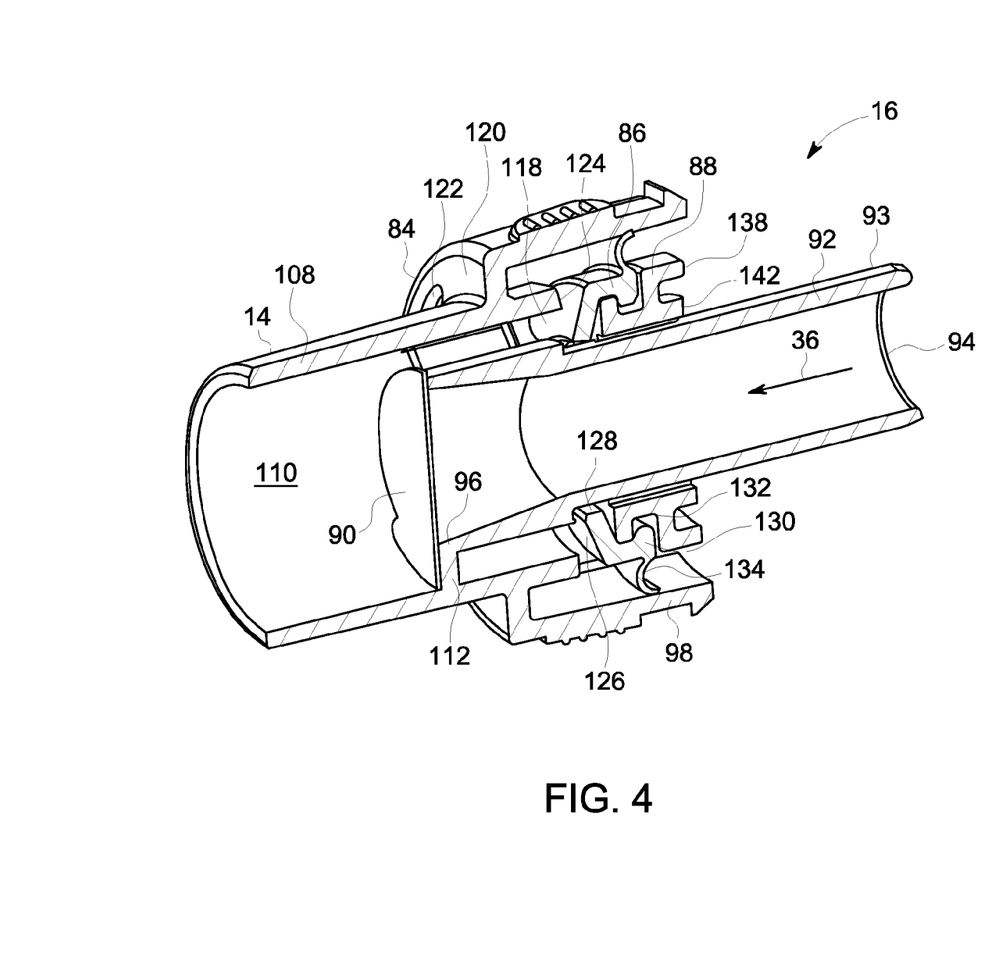
FIG. 4 is a section view of the detachable inspiratory relief valve.

The details of the removable relief valve assembly 16 are best illustrated in FIG. 4. The relief valve assembly 16 is a preassembled unit that can be selectively connected to and disconnected from the ventilator as a unitary element. In general, the relief valve assembly 16 consists of a connector housing 84, a sealing member 86, a support collar 88, and a one-way valve member 90. The individual components shown in FIG. 4 are preassembled and can be attached to the ventilator as a single unit.

Figure 5:
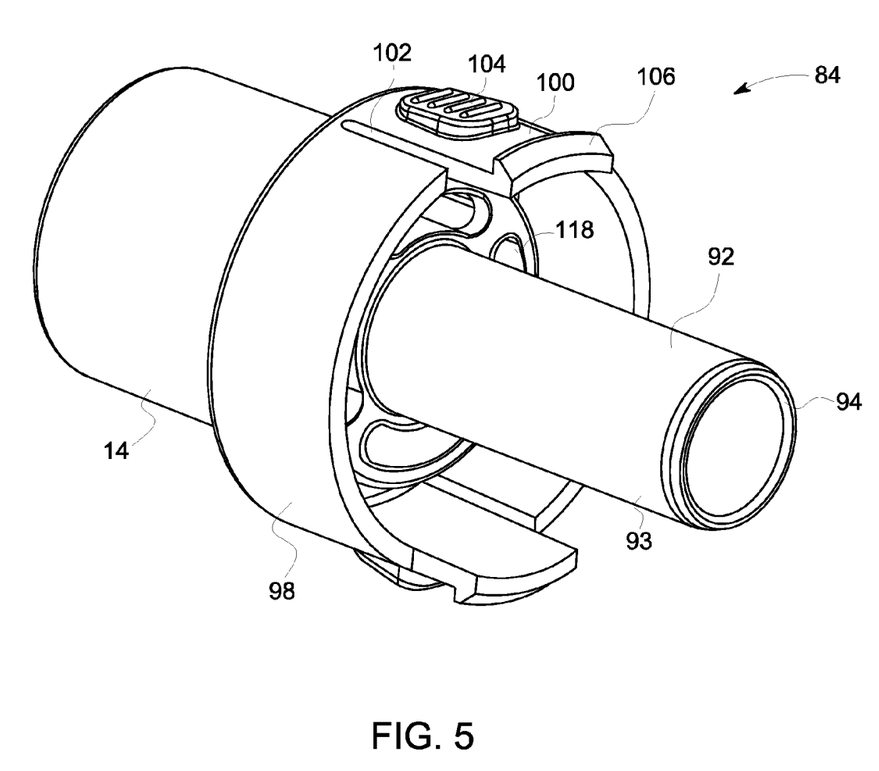
FIG. 5 is a back isometric view of a portion of the inspiratory relief valve.

As illustrated in FIGS. 4 and 5, the connector housing 84 includes an engagement tube 92 that has a generally smooth cylindrical outer surface 93 extending from a first end 94 to a second end 96. The second end 96 of the engagement tube 92 is covered by the one-way valve member 90. The one-way valve member 90 is configured such that the one-way valve member allows the flow of gas in only the direction shown by arrow 36. In the embodiment illustrated, the valve member 90 is a flap valve formed from a resilient silicone material. The pressure of gas flowing in the direction of arrow 36 causes the valve member 90 to open while the outer edge of the engagement tube 92 prevents the valve member 90 from opening in the opposite direction. The valve member 90 thus prevents the back flow of gases from the patient into the ventilator.

Referring now to FIG. 5, the connector housing 84 includes a depending attachment collar 98 that includes a pair of spaced locking tabs 100. Each of the locking tabs are separated from the remaining portions of the attachment collar 98 by a pair of removed areas 102 that allow the locking tabs 100 to flex relative to the remaining portions of the attachment collar 98. Each of the locking tabs 100 include a grip portion 104 that provides a visual indication to the user where the user can grasp the attachment collar 98 to cause movement of the locking tabs 100.

Each locking tab includes an extending locking finger 106. As illustrated in FIG. 3, the finger 106 engages the projection 82 on the locking ring 22 to secure the relief valve assembly 16 in the position shown. Depression of each of the pair of locking tabs 100 releases the finger 106 from the projection 82 such that the relief valve assembly 16 can be removed.

Referring back to FIG. 4, the connector housing 84 further defines a connector tube 14 that is defined by an outer wall 108. The outer wall 108 defines an internal flow passageway 110. As described previously, the connector tube 14 is sized to receive a breathing tube such that breathing gases can be transmitted from the ventilator to the patient.

Figure 7:
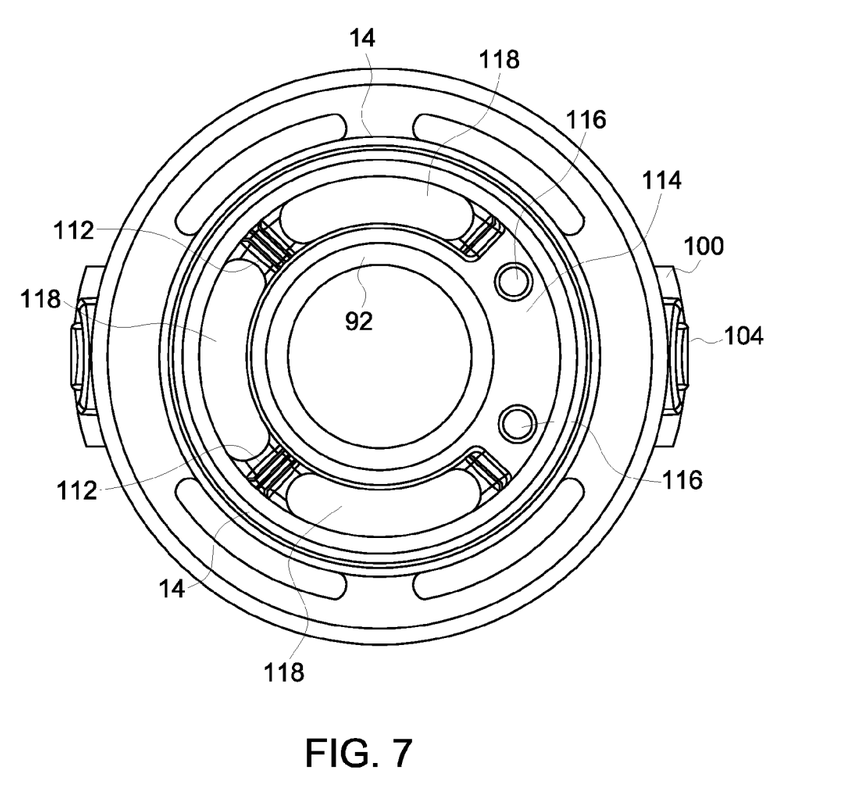
FIG. 7 is a front view of the valve housing.

As illustrated in FIGS. 4 and 7, the second end 96 of the engagement tube 92 is spaced radially from the outer wall 108 of the connector tube 14 by a series of spaced webs 112 along with the valve member mounting platform 114. The mounting platform 114 includes a pair of openings 116 that receives extended legs (not shown) formed as a portion of the valve member 90.

As illustrated in FIG. 7, a plurality of relief ports 118 are formed between the outer wall of the engagement tube and the inner wall of the connector tube 14. The relief ports 118, when left open as shown in FIG. 7, allow breathing gas, or any other type of gas, to pass out of the relief ports and be vented to atmosphere. The relief ports 118 can be clearly seen in FIG. 5 as providing a flow passageway for gas to exit into the open interior defined by the attachment collar 98.

Figure 6:
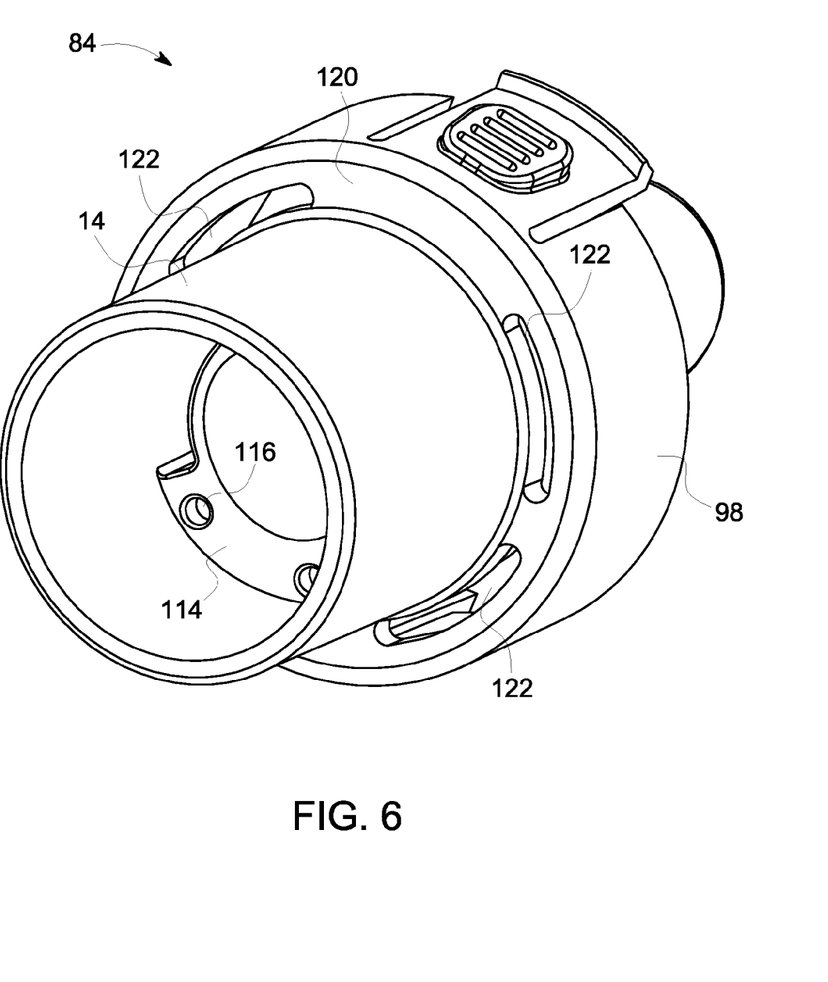
FIG. 6 is a front isometric view of the valve housing.

Referring now to FIG. 6, the outer wall that defines the attachment collar 98 is connected to a perpendicular face surface 120 of the connector housing 84. The face surface 120 extends between the outer wall of the connector tube 14 and the outer surface that defines the attachment collar 98. A series of vents 122 are formed in the face surface 120 to allow gas to exit from the interior defined by the attachment collar 98.

Figure 9:
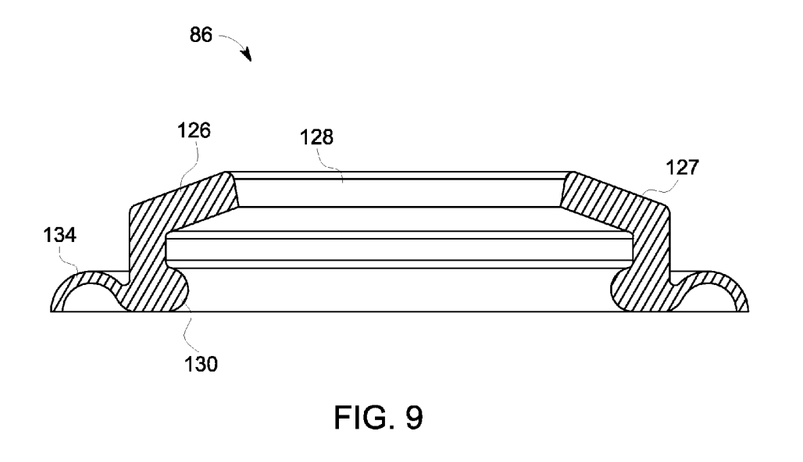
FIG. 9 is a section view of the sealing gasket that forms part of the inspiratory relief valve.

As best shown in FIGS. 4 and 9, the relief valve assembly 16 includes the sealing member 86. The sealing member 86 surrounds the outer surface of the engagement tube 92 and is movable toward and away from the inner end 124 of the connector tube 14, which includes the series of relief ports 118. The sealing member 86 is movable into contact with the inner end 124 to seal each of the relief ports 118. When the sealing member 86 is moved away from the inner end 124, gas is able to pass through the relief ports 118 and be vented to atmosphere through the vents 122 formed in the face surface 120.

As illustrated in FIG. 9, the sealing member 86 includes a generally conical sealing surface 126 formed as part of a resilient projection 127 that surrounds a center opening 128. The center opening 128 surrounds the engagement tube 92 such that the sealing member 86 is movable along the engagement tube 92. The sealing member 86 includes a resilient projection 130 that is received within a recessed groove 132 formed in the support collar 88, as illustrated in FIG. 4. The interaction between the resilient projection 130 and the groove 132 holds the sealing member 86 in place.

Referring back to FIG. 9, the resilient projection 127 has a conical configuration that urges the sealing member into the condition shown. The projection 127 generates a resilient bias force that urges sealing surface 126 of the sealing member 86 to the retracted condition, as shown in FIG. 4. When the sealing member 86 is urged upward, the upward motive force overcomes the bias force created by the resilient projection 127 so that the conical feature becomes flat. However, when the extending force is removed, the projection 127 flexes to cause the sealing member 86 to return to the condition shown in FIG. 4. The sealing member 86 includes an extending outer lip 134 that frictionally engages the inner surface of the attachment flange 98 to prevent the sealing member 86 and the support collar 88 from falling out of the connector housing 84 when the relief valve assembly is separated from the ventilator. In the preferred embodiment of the disclosure, the sealing member 86 is formed from a resilient silicone material. However, it is contemplated that various other materials could be utilized while operating within the scope of the present disclosure.

Referring back to FIG. 3, when the relief valve assembly 16 is installed onto the locking ring 22, the first end 94 of the engagement tube 92 is received within the second end 50 of the bias force assembly 34. The second sealing member 48 engages the outer surface of the engagement tube 92 to provide a gas-tight seal therebetween.

In the installed condition shown in FIG. 3, outer end 136 of the adjustment collar 58 contacts an outer rim 138 of the support collar 88. At the same time, intermediate collar 140 is entrapped between the inner rim 142 and the bias force assembly 34.

During normal operating conditions, the ventilator rotates the drive disk 62 to an operating position such that the bias spring 52 exerts a force on the contact surface 56 of the adjustment collar 58 to move the adjustment collar toward its extended, first position. During this movement, the adjustment collar 58 exerts a force on the sealing member 86 which causes the sealing member 86 to block each of the relief ports 118. In this position, the sealing member 86 prevents the flow of gas through the relief ports 118.

During operation of the ventilator, if the ventilator detects an unacceptable increase in pressure in the breathing tube, which may be a result of an occlusion in the breathing tube, the ventilator rotates the drive disk 62 to move the adjustment collar 58 against the bias force of the bias spring 52. When the adjustment collar 58 moves toward the second, retracted position, the bias force created by the sealing feature 126 moves the sealing member 86 away from the plurality of relief ports 118, as shown in FIG. 4. In this manner, the ventilator can selectively open the relief ports 118 upon detection of an over-pressure situation in the breathing tube.

When the ventilator determines that the over-pressure condition no longer exists, the ventilator rotates the drive disk 62 to again allow the bias spring 52 to exert the required bias force to cause the sealing member 86 to close each of the relief ports. In this manner, the ventilator can selectively open and close the relief ports by rotation of the drive disk 62.

As can be understood in FIG. 4, the entire relief valve assembly 16 can be removed and either replaced or sanitized as desired. The ability of the entire relief valve assembly to be removed and replaced as a single unit enhances the ability of an operator to quickly and easily replace the relief valve assembly while insuring that the operation of the ventilator in conjunction with the relief valve assembly is maintained.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A relief valve assembly for use with a ventilator having an inspiratory port for delivering breathing gas to a patient, comprising:

a connector housing having an attachment feature for removably attaching the connector housing to the ventilator, the connector housing including an engagement tube received in the inspiratory port to receive the breathing gas and a connector tube surrounding a distal end of the engagement tube, wherein at least one relief port is formed between the connector tube and the engagement tube;

a one-way valve positioned at the distal end of the engagement tube to permit one-way flow of the breathing gas from the engagement tube to the connector tube; and a sealing member selectively movable along the engagement tube into and out of contact with the at least one relief port.

2. The relief valve assembly of claim 1 wherein the relief valve assembly is installed on and removed from the ventilator as a single unit.

3. The relief valve assembly of claim 1 wherein the sealing member is movable into and out of sealing contact with the at least one relief port at the control of the ventilator.

4. The relief valve assembly of claim 1 wherein the sealing member surrounds the engagement tube.

5. The relief valve assembly of claim 1 wherein the attachment feature includes at least one locking tab that engages a locking ring on the ventilator to secure the connector housing to the ventilator.

6. The relief valve assembly of claim 1 wherein the at least one relief port provides fluid communication between the connector tube and atmosphere.

7. The relief valve assembly of claim 6 wherein the connector tube is sized to receive a breathing tube such that the breathing tube is connected to atmosphere through the at least one relief port when the sealing member is moved out of contact with the at least one relief port.

8. The relief valve assembly of claim 1 wherein the sealing member includes a resilient outer projection that urges the sealing member away from the at least one relief port when the sealing member is positioned within the connector housing.

9. An interface assembly for use between an inspiratory port of a ventilator and a breathing tube for use with a patient, wherein the interface assembly provides fluid communication for a flow of breathing gas from the inspiratory port to the breathing tube, comprising:

an adjustment collar contained within the ventilator and selectively movable between a first position and a second position;

a connector housing having an attachment feature for removably attaching the connector housing to the ventilator, the connector housing including an engagement tube received in the inspiratory port to receive the breathing gas flow and a connector tube surrounding a distal end of the engagement tube, wherein at least one relief port is formed between the connector tube and the engagement tube;

a one-way valve positioned at the distal end of the engagement tube to permit one-way flow of the breathing gas from the engagement tube to the connector tube; and a sealing member coupled to the adjustment collar, wherein the sealing member is in sealing engagement with the at least one relief port when the adjustment collar is in the first position and the sealing member is spaced from the at least one relief port when the adjustment collar is in the second position.

10. The interface assembly of claim 9 wherein the interface assembly is installed and removed from the ventilator as a single unit.

11. The interface assembly of claim 9 wherein the sealing member surrounds the engagement tube and is movable therealong through the movement of the adjustment collar.

12. The interface assembly of claim 9 wherein the attachment feature includes at least one locking tab that engages a locking ring formed on the ventilator.

13. The interface assembly of claim 9 wherein the at least one relief port provides fluid communication between the connector tube and atmosphere.

14. The interface assembly of claim 9 further comprising a bias spring positioned to exert a bias force on the adjustment collar to urge the adjustment collar into the first position.

15. The interface assembly of claim 14 further comprising a drive member positioned in the ventilator and selectively operable to move the adjustment collar to the second position against the bias force from the bias spring.

16. The interface assembly of claim 15 wherein the drive member is operated upon the ventilator detecting an occlusion in the breathing tube.

17. The relief valve assembly of claim 9 wherein the sealing member includes a resilient outer projection that urges the sealing member away from the at least one relief port when the sealing member is positioned within the adjustment collar.

18. A method of relieving pressure in a breathing tube receiving a breathing gas from an inspiratory port of a ventilator comprising the steps of:

removably attaching a relief valve assembly to the ventilator, the relief valve assembly including a connector housing including an engagement tube received in the inspiratory port and a connector tube surrounding a distal end of the engagement tube wherein at least one relief port is formed between the connector tube and the engagement tube;

selectively moving an adjustment collar relative to the connector housing between a first position and a second position, wherein a sealing member of the relief valve assembly moves into contact with the at least one relief port to prevent the flow of gas to atmosphere when the adjustment collar is in a first position and the sealing member is moved away from the at least one relief port when the adjustment collar is in a second position.

19. The method of claim 18 wherein the ventilator moves the adjustment collar to the second position upon the ventilator detecting an over-pressure condition in the breathing tube.

20. The method of claim 19 further comprising the step of applying a bias force on the adjustment collar to bias the adjustment collar into the first position, wherein the ventilator moves the adjustment collar to the second position against the bias force.

* * * * *